(12) United States Patent
Puritch et al.

(10) Patent No.: US 6,852,329 B2
(45) Date of Patent: Feb. 8, 2005

(54) INGESTIBLE MOLLUSCICIDE

(75) Inventors: George S. Puritch, Saanichton (CA); Andreas Prokop, Hamelin (DE); David S. Almond, Victoria (CA); Robert Matson, Victoria (CA)

(73) Assignee: W. Neudorff GmbH KG (DE)

( * ) Notice: Subject to any disclaimer, the term of this patent is extended or adjusted under 35 U.S.C. 154(b) by 0 days.

(21) Appl. No.: 10/289,165

(22) Filed: Nov. 6, 2002

(65) Prior Publication Data

US 2003/0118625 A1 Jun. 26, 2003

Related U.S. Application Data

(60) Provisional application No. 60/332,720, filed on Nov. 14, 2001.

(51) Int. Cl.$^7$ ............................................. A01N 25/32
(52) U.S. Cl. ..................... 424/406; 424/84; 424/405; 424/408; 424/409; 424/410; 424/421; 424/485; 424/488; 424/630; 424/646; 424/647; 424/648
(58) Field of Search ................. 424/409, 405, 424/408, 84, 646–648, 630–638, 639, 640, 641, 643, 682, 421, 485, 488, 406

(56) References Cited

U.S. PATENT DOCUMENTS 5,733,858 A * 3/1998 Wilson et al. ............... 30/360
6,093,416 A * 7/2000 Young ........................ 424/409

FOREIGN PATENT DOCUMENTS

| JP | 9136807 | 5/1997 |
| WO | WO 89/01287 | 2/1989 |
| WO | WO 96/05728 | 2/1996 |
| WO | WO 97/26789 | 7/1997 |
| WO | WO 99/39576 | 8/1999 |

OTHER PUBLICATIONS

Hacks, Chemical Dictionary p 687, 80.*

Prov et al: "Testing iron, zinc, and manganese complexes with ethylenediaminedsuccinic and iminodisuccinic acides in clorotic vineyards" STN CAPLUS, XP002100085 *abstract*.

"Iminodisuccinate: Iminodisuccinic Acid Sodium Salt," published by Bayer Corporation Industrial Chemicals Division, 100 Bayer Road, Pittsburgh PA 15205–9741 (no date), Pre Nov. 19, 2001.

* cited by examiner

*Primary Examiner*—Neil S. Levy
(74) *Attorney, Agent, or Firm*—Nutter McClennen & Fish LLP

(57) ABSTRACT

An effective, readily ingested molluscicidal bait poison includes a mollusc bait and a second component. The second component can contain a transition metal compound and a complexing agent, and/or the complex of a transition metal compound and a complexing agent. The complexing agent is preferably iminodisuccinic acid (IDS), including sodium IDS (IDS Na-Salt), iminodifumaric acid (IDF), iminoditartaric acid (IDT), iminodimaleic acid (IDMAL), ethylenediaminedifumaric acid (EDDF), ethylenediaminedimalic acid (EDDM), iminodimalic acid (IDM), ethylenediaminedltartaric acid (EDDT), ethylenediaminedimaleic acid (EDDMAL), and salts thereof.

22 Claims, No Drawings

INGESTIBLE MOLLUSCICIDE

REFERENCE TO RELATED APPLICATION

This application claims priority from U.S. Provisional Patent Application Ser. No. 60/332,720, filed on Nov. 14, 2001, entitled "Ingestible Molluscicide," which is expressly incorporated by reference herein.

FIELD OF THE INVENTION

The present invention relates to ingestible compositions for the control of terrestrial molluscs.

BACKGROUND OF THE INVENTION

Terrestrial pulmonate gastropods, slugs and snails (collectively, molluscs) are significant plant pests that affect commercial agriculture and horticulture and domestic gardens. These molluscs are omnivorous and consume large amounts of vegetative materials during their daily foraging. Consequently, they can seriously damage vegetable gardens and even plant crops during all phases of the growing cycle. Because of their destructive potential, control measures must be employed to ensure adequate protection of the growing plants from damage by terrestrial molluscs.

A wide variety of approaches have been used to try to combat pest molluscs. Perhaps the most common is the use of poisonous compounds called molluscicides. Molluscicides include a diversity of chemical compounds such as table salt (NaCl), calcium arsenate, copper sulfate, and metaldehyde. Molluscicides fall into two major groups, depending upon their mode of action: contact poisons and ingestible (or bait) poisons.

Contact poisons are molluscicides that, to be effective, must come into physical contact with the exterior of the mollusc, either by external application or through the action of the mollusc traversing a molluscicidal composition placed on the ground. The contact molluscicide is picked up by the proteinaceous slime coat of the mollusc and it builds up in the body of the mollusc until a lethal proportion is reached. One of the major drawbacks of contact molluscicides is that they have little effect if the molluscs do not physically contact the active chemical agent. If the molluscs are hidden or migrate into an area after a contact molluscicide is spread, the molluscs are unaffected. For these reasons, contact-acting mollusc poisons generally are considered to be unreliable.

Heavy metals, including zinc, aluminum, copper and iron, are all toxic to molluscs and are examples of compounds known to be effective molluscicides when used as contact poisons in the form of salts or chelates. See, Henderson, et al. *Crop Protection* (1990), 9, 131–134 and Henderson, et al., *Ann. Appl. Biol.* (1990), 116, 273–278.

Ingestible (or bait) mollusc poisons are those that must be ingested by a mollusc in order to be lethal. This type of mollusc poison tends to be preferred over contact poisons only because contact poisons, which rely upon passive acquisition of the active ingredient, are not considered to be reliable. One challenge associated with the development of effective bait molluscicides is to prepare a composition that is both palatable to the mollusc and effective as a lethal poison. Obviously, a sufficient quantity of the poison must be ingested to reach the lethal threshold. Often, compositions that are palatable to the mollusc are not effective as a lethal poison, while compositions that are quite potent and lethal are not readily ingested by molluscs. Many contact poisons, such as aluminum sulfate, copper sulfate and borax, are useless as ingestible poisons because they are not palatable to molluscs, and the molluscs do not ingest a lethal dose of these compounds. Ingestible poisons must be sufficiently palatable to the mollusc so that they will be consumed in lethal amounts, but the composition must also be slow acting enough to prevent the mollusc from becoming sick or cause it to cease feeding.

Typical problems associated with the development of compounds for the effective control of molluscs are discussed by Henderson, et al. in *Aspects of Appl. Biol.* (1986) 13, 341–347. This publication recognizes that although many compounds are known to be poisonous to molluscs, there is considerable difficulty in delivering the poison to the mollusc either as a bait or as a contact poison. The potential toxicity of a compound is irrelevant if molluscs will not consume a lethal dose of a bait poison.

Even if the molluscs will consume the bait, however, not all metal-containing compounds, e.g., metal chelates, will be effective. All metal chelates, even those in the same family, are uniquely different with respect to their biological effect on molluscs; not all such metal chelates are effective to kill molluscs even when the molluscs are injected with lethal doses of iron or similar metal. The effect of metal chelates on molluscs is a result of a unique physical reaction. The particular reasons why certain metal chelates are effective and others are not are unknown.

Accordingly, there remains a need for an effective ingestible poison for molluscs that is both palatable to molluscs and that does not pose a threat to the environment, crops, animals and other non-pests.

SUMMARY OF THE INVENTION

The invention provides an effective ingestible poison that is lethal to terrestrial molluscs. The composition is comprised of constituent compounds which do not pose any significant threat to the environment, plants, animals and other non-pests. Preferably, the constituent compounds are biodegradable. In one embodiment the composition combines a carrier, such as a bait, with a second component containing a transition metal compound and a complexing agent. The transition metal compound can be a transition metal protein, a transition metal carbohydrate, e.g., a sugar, or a transition metal salt. Suitable complexing agents include, for example, iminodisuccinic acid (IDS), iminodifumaric acid (IDF), iminoditartaric acid (IDT), iminodimaleic acid (IDMAL), ethylenediaminedifumaric acid (EDDF), ethylenediaminedimalic acid (EDDM), iminodimalic acid (IDM), ethylenediaminediartaric acid (EDDT), and ethylenediaminedimaleic acid (EDDMAL).

In another embodiment the composition comprises a carrier bait and a second component formed from the complex of a transition metal compound and a complexing agent. In still another embodiment, the second component is a compound that has a transition metal compound associated with a complexing agent; that is, the transition metal compound does not require that a true complex be formed between the transition metal and the complexing agent.

In another aspect, the present invention provides methods for exterminating molluscs by providing a molluscicidal composition which is applied to an area infested with molluscs and allowing the molluscs to ingest the molluscicidal composition. The molluscicidal composition can include a transition metal compound, such as a transition metal protein, carbohydrate, or salt, and a complexing agent. In another embodiment, the molluscicidal composition is formed from the complex of a transition metal compound and a complexing agent. The composition can also include a carrier material edible to molluscs.

DETAILED DESCRIPTION OF THE INVENTION

The present invention provides a bait poison that is effective against terrestrial molluscs. In one embodiment the composition of the invention combines a carrier, such as a mollusc bait, with a second component. The second component can contain a transition metal compound and a complexing agent, preferably a chelating agent, or alternatively the second component can be formed from the complex of a transition metal compound and a complexing agent, or the chelate of a transition metal compound and a chelating agent. The composition is preferably biodegradable.

In one embodiment of the present invention, an edible stomach-acting bait poison is formed from a carrier material and a second component containing a transition metal compound and a complexing agent. The term "transition metal" is recognized by those having ordinary skill in the art and it is intended to include those metals which can exist with two or more valences.

Suitable transition metals compounds for use in the second component include, for example, transition metal proteins, transition metal carbohydrates, and transition metal salts. The transition metal compounds can be present in one or more of their valences. Examples of suitable transition metal compounds are saccharated transition metals, transition metal albuminates, transition metal ammonium citrates, transition metal chlorides, transition metal citrates, transition metal gluconates, transition metal lactates, transition metal phosphates, transition metal pyrophosphates, transition metal nitrates, transition metal sulfates, transition metal stearates, and transition metal tartrates.

Preferred transition metals include iron (ferric or ferrous), copper (cupric or cuprous), zinc and aluminum. In an exemplary embodiment, the transition metal compound is a simple iron compound and can be selected from any one of a number of iron salt compounds, including iron proteins, iron carbohydrates, and iron salts. The iron compound can be present in its iron (II) state (ferrous), as well as in its iron (III) state (ferric). Examples of suitable simple iron compounds are saccharated ferric oxide, ferric albuminate, ferric ammonium citrate, ferric chloride, ferric citrate, ferrous gluconate, ferrous lactate, ferric phosphate, ferrous phosphate, ferric pyrophosphate, ferric nitrate, ferrous sulfate, ferric stearate, ferrous stearate, and ferric tartrate. Suitable simple iron compounds are commercially available from a variety of sources, including Dr. Paul Lohmann GmbH KG of Emmerthal, Germany.

Preferably, the molar ratio of the transition metal in the transition metal compound to the complexing agent is in the range of 1:0.02 to 1:60, and more preferably is in the range of 1:0.02 to 1:20. The transition metal compound preferably is present within the composition at an amount such that the transition metal concentration in the composition is in the range of about 200 to 90,000 ppm. More preferably, the transition metal compound should be present in an amount such that the transition metal concentration in the composition is in the range of 500 to 10,000 ppm. In a preferred embodiment, the transition metal is iron.

The second component further includes a complexing agent, which can be a biodegradable chelating agent. Suitable complexing agents include, but are not limited to, iminosuccinic acid (IDS), iminodifumaric acid (IDF), iminoditartaric acid (IDT), iminodimaleic acid (IDMAL), ethylenediaminedifumaric acid (EDDF), ethylenediaminedimalic acid (EDDM), iminodimalic acid (IDM), ethylenediamineditartaric acid (EDDT), and ethylenediaminedimaleic acid (EDDMAL).

In an exemplary embodiment, the complexing agent is D,L-aspartic acid, N-(1,2-dicarboxyethyl), tetrasodium salt, which is a biodegradable chelating agent also referred to as iminodisuccinic acid sodium salt (hereinafter IDS Na-salt). IDS Na-Salt is commercially available from Bayer Corporation, of Pittsburgh, Pa. The chelating agent is available in both a solution form and a solid form. The principal minor components of IDS Na-salt are the sodium salts of aspartic, fumaric, and malic acids, all of which are compounds that are not only found in nature but often used in beverages and foods. IDS Na-Salt is particularly advantageous in that it is believed to enhance absorbability and distribution of the metal within the mollusc's system.

The IDS Na-Salt is prepared by treating maleic anhydride with water, ammonia, and sodium hydroxide. The chemical formulation is as follows:

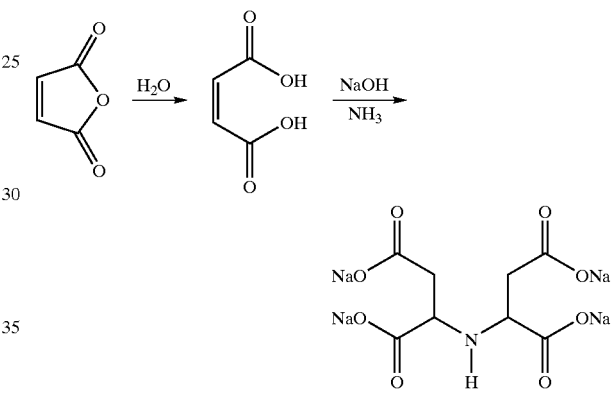

No gaseous or other waste products are formed during the preparation of IDS Na-Salt.

The IDS Na-salt preferably is present in the composition at a concentration in the range of about 2000 to 140,000 ppm. More preferably this component is present at about 7,000 to 120,000 ppm.

In another embodiment, the molluscicidal composition includes a second component formed from the complex of a transition metal compound and a complexing agent. Suitable transition metal compounds and complexing agents are disclosed above. By way of non-limiting example, the complexing agent can be a chelating agent, in which case the second component will be a chelate formed from the transition metal compound and the chelating agent.

The term "complex" is recognized by those having ordinary skill in the art and is intended to include those compounds which have a physical interaction/attraction between a transition metal or its salt and a complexing agent. In certain instances, where the complexing agent is a chelating agent, for example, the carboxylate(s) of the chelating agent utilize only the transition metal or its salt as a counterion. Alternatively, the carboxylate(s) of the chelating agent may only partially coordinate with the transition metal or its salt as a counterion and are associated with other counterions. Preferably, the transition metal, e.g., iron, concentration in the complex is in the range of about 200 to 90,000 ppm.

The term "chelate" is understood by those having ordinary skill in the art and is intended to include those compounds where the metal ion or metal salt is coordinated with/through the lone pairs of electrons of the chelating agent through ionic and/or van der Waals interactions. Typically in a chelate, the chelating agent utilizes only the transition metal or its salt as a counterion for each carboxylate without any other counterions present.

The terms "association" or "associate" are understood by those having ordinary skill in the art and are intended to include those interactions between a metal ion or salt and the complexing agent, or a derivative of the complexing agent, through, for example, charge-charge interactions. An associated chelate, for example, may not qualify as a true chelate in that one or more of the carboxylate(s) of the chelating agent may not coordinate with the metal but may coordinate with another counterion. Therefore, the terms "complex" and "chelate" as used herein are intended to include either complexes/chelates, associations of constituents, or combinations of both.

Complexes can be prepared by methods known in the art. For example, a sample of a complexing agent derivative or a salt thereof can be dissolved in an aqueous or organic solution. An excess of metal salt, e.g., iron chloride, iron nitrate, etc., can be added to the solution. The amount of metal salt added can vary depending upon the solvent, the temperature of the solution, metal and complexing agent derivative. Generally, the solution is warmed so that the solution can be saturated with the complexing agent derivative and metal salt. Upon cooling, the complex, e.g., a chelate or an associated compound of metal and ligand, precipitates and is collected. Alternatively, a non-solvent can be added to the solution to facilitate precipitation of the complex.

The phrase "effective amount" is recognized by those skilled in the art and is intended to mean that amount of one or more components required to cause mollusc mortality. For example, the ranges indicated supra, are considered effective for treating infestation of molluscs in an afflicted area. The effective amount is that amount of a composition of the invention necessary or sufficient to perform its intended function within a mollusc, e.g., to cause expiration. An effective amount of the composition can vary according to factors such as the amount of the causative agent already present in the mollusc and the weight of the mollusc. One of ordinary skill in the art would be able to study the aforementioned factors and make a determination regarding the effective amount of the compositions without undue experimentation. An in vitro or in vivo assay also can be used to determine an "effective amount" of the composition described supra. The ordinarily skilled artisan would select an appropriate amount of the compositions for use in an appropriate assay. An effective amount of the compositions of the invention preferably eliminates at least about 20%, more preferably by at least about 60%, even more preferably by at least about 80%, and still more preferably by at least about 99% or greater of the molluscs relative to untreated subjects.

The carrier component of the molluscicidal composition of the invention is one that must be readily consumed by molluscs. A variety of mollusc baits are well known and may be used in the compositions of the present invention. Such baits include agar, potato dextrose agar, sugar beet, gelatin, oil cake, pet food, wheat, soya, oats, corn, rice, fruits, fish by-products, sugars, coated vegetable and cereal seeds, casein, blood meal, bone meal, yeast, paper products, clays, fats, and a variety of cereals, including wheat cereal. A preferred bait is wheat cereal which is commercially available from various sources.

The molluscicidal bait composition of the invention can also include additional formulation enhancing additives. Such additives include preservatives or anti-microbial agents, phagostimulants, water-proofing agents, and taste altering additives.

A variety of preservatives can be used effectively with this molluscicidal bait composition. Examples of preferred preservatives include Legend MK®, available from Rohm & Haas Company of Philadelphia, Pa. and CA-24, available from Dr. Lehmann and Co. of Memmingen/Allgäu, Germany. Preservatives such as these can normally be mixed with water to form a stock solution to be added to the formulation at a concentration in the range of about 10–750 ppm.

Phagostimulants can be added to the composition to attract molluscs and to induce molluscs to feed upon the composition. A variety of phagostimulants can be used, including sugars, yeast products and casein. Sugars, such as sucrose, are among the more preferred phagostimulants. These additives are normally incorporated within the composition in a dry form. Typically, they can be added to the composition at about 1 to 2.5% by weight of the total composition.

Waterproofing agents, which can also act as binders, can be added to the composition to improve the weatherability of the molluscicidal bait. These are typically water insoluble compounds such as waxy materials and other hydrocarbons. Examples of suitable waterproofing agents are paraffin wax, stearate salts, beeswax, and similar compounds. One preferred wax compound is PAROWAX®, available from Conros Corp. of Scarborough, Ontario, Canada. Waterproofing agents can be incorporated into the composition, in dry form, at about 5 to 12% by weight of the total composition.

It is also desirable to include within the molluscicidal bait taste altering compounds that render the composition unpalatable to animals. Exemplary compositions include those having a bitter taste. Suitable compounds that are commercially available include BITREX, available from McFarlane Smith Ltd. of Edinburgh, Scotland. These compounds typically are added at very low concentrations. For example, a 0.1% BITREX solution can typically be added to the composition at about 1 to 2% by weight of the total composition.

The molluscicidal bait of this invention typically is used in dry form and many of the constituent ingredients of the composition are included in dry form. However, it is useful to include a sufficient amount of water within the composition to form a dough so that the ingredients can be more easily formed. Water is typically added at about 15 to 60% by weight of the total composition. The water, however, typically is driven off by heating and drying the molluscicidal bait before it is used.

As noted above, the compositions of the present invention are typically used in a dry, spreadable form such as powders, granules, cubes, or pellets. The composition may be spread on or around areas infested by molluscs as well as in areas in which mollusc infestation is to be prevented.

In another aspect, the present invention provides methods for exterminating molluscs by providing a molluscicidal composition, described supra, which is applied to an area infested with molluscs, and allowing the molluscs to ingest the molluscicidal composition. In this manner, unwanted mollusc pests are eliminated from the treated area In one embodiment the composition of the invention combines a carrier, such as a mollusc bait, with a second component. The second component can contain a transition metal compound and a complexing agent, preferably a chelating agent, or alternatively the second component can be formed from the complex of a transition metal compound and a complexing agent, or the chelate of a transition metal compound and a chelating agent.

Not to be limited by theory, it is believed that the combination of the carrier, a transition metal and a complexing agent, or the complex of a transition metal and a complexing agent, increases the toxic activity of the metal within the mollusc. It is believed that with the carrier, the complexing agent provides an effect in combination with the metal, such that the ingestion, absorption and distribution of the transition metal, e.g., iron, is enhanced. The distribution of the metal and increased concentration of the metal within the mollusc blocks mollusc feeding, thereby enhancing mollusc mortality. Therefore, one characteristic of the compositions of the invention is that the absorption and distribution of the metal within the mollusc body can be altered by the complexing agent, thereby rendering the metal toxic to molluscs.

An advantage of the molluscicidal compositions of the present invention is that the second component, when combined with a carrier, exhibits good mortality against terrestrial molluscs and is readily consumed by terrestrial molluscs. A further advantage of the compositions of the present invention is that the constituents are environmentally safe and pose no threat to humans, animals or other non-pests. The composition is not only lethal to molluscs, but molluscs are also poisoned to the extent that they cease feeding upon plants after consuming the composition.

In another embodiment of the present invention, the complexing agent is preferably biodegradable. Chelating agents, or chelate-like agents, are used in a variety of applications including, fertilizers, animal feeds and herbicides. Consequently, some applications, including bait compositions, result in chelates entering the environment. It is therefore desirable that complexes, and in particular chelates, used in the mollusc poison compositions degrade after use. Biodegradability, that is susceptibility to degradation by microbes, is particularly useful because the microbes are generally naturally present in environments into which the chelates may be introduced. Thus, the complexing agents useful in the mollusc baits of the invention provide an advantage by degrading quickly and easily.

Dry molluscicidal compositions according to the present invention can be prepared as follows. A suitable amount of the active ingredient can be blended in dry form with a dry mollusc bait, such as wheat flour. Thereafter, other dry ingredients (such as phagostimulants and waterproofing agents) can be blended and mixed with the bait. Next, suitable amounts of liquid additives (such as preservatives, taste altering additives and water) can be added to the dry mixture to form a dough. The bait is preferably covered, such as with plastic wrap, and heated. One preferred heating technique is by heating in a microwave oven for 30 seconds to 10 minutes. After heating, the dough can be processed in a food grinder to obtain strands of the bait material, which can be dried, at elevated or ambient temperatures, and made into a desired form, such as powder, pellets or granules.

An exemplary formulation of a suitable mollusc bait is as follows:

|  | INGREDIENT | QUANTITY |
| --- | --- | --- |
| DRY COMPONENTS | Wheat flour | 78.97 g |
|  | IDS Na-salt | 9.00 g |
|  | Ferric sulfate | 1.68 g (0.4% Fe) |
|  | Paraffin Wax | 8.00 g |
|  | Sucrose | 2.10 g |
| LIQUIDS | BITREX | 0.15 g |
|  | Legend MK ® | 0.10 g (15 ppm ai) |
|  | Water | 30.00 g |
|  | TOTAL | 130.00 g |

The molluscicidal composition of the present invention should be effective against a variety of terrestrial molluscs including Ariolimax spp.; Arion species including, *Arion ater, A. hortensis, A. rufus, A. circumscriptus, A. empericorum*; Deroceras spp.; Agriolimax spp.; Prophysaon spp.; *Helix pomata*; and *Cepaea nemoralis*.

In another embodiment, molluscicidal baits can be prepared as follows. First, transition metal compounds, e.g., iron carbohydrate or iron salts, can be dry blended into a cereal flour (wheat) at between about 1000 to 10,000 ppm metal wt/wt. Dry IDS Na-salt can then be added to the flour on an equal molar level to the amount of transition metal added. The molar ratio of a metal to complexing agent can vary and can be in the range of about 1:0.02 to 1:60.0. The complexing agent can be added to the mixture while continually stirring. Other ingredients can also be added to the mixture, such as antimicrobials (e.g., Legend® ), waterproofing agents, and phagostimulants (e.g., sugar). Water soluble additives can be dissolved in water and added to the dry mixture. The dough can be thoroughly mixed in a grinding device and extruded in the form of noodles. The resulting bait can then be dried at 40° C. for 24 hours prior to testing.

In yet another embodiment, a molluscicidal composition can be prepared as follows. First, a transition metal/complexing agent complex can be dry blended into a cereal flour (wheat) at between about 1000 to 10,000 ppm metal wt/wt. Other ingredients can be added to the mixture, such as, antimicrobials (e.g., Legend® ), waterproofing agents, and phagostimulants (e.g., sugar). Water soluble additives can be dissolved in water and then added to the dry mixture. The dough can be thoroughly mixed in a grinding device and extruded in the form of noodles. The resulting bait can be dried at 40° C. for 24 hours prior to testing.

The following non-limiting examples serve to further illustrate the present invention.

EXAMPLE 1

Iron IDS was made by complexing the liquid NaIDS (Baypure CX100/34) with iron sulfate. The mixture was then dry blended into 96.08% cereal flour (wheat) and sugar, and prepared as described above.

Two test tubs were set up, each containing 10 *Arion ater* and one young potted lettuce plant. Compost soil was used to cover the tub bottoms. The slugs were collected and added to the tubs the same day. Each tub received 7.5 grams of bait scattered over the soil. The tubs were kept outside in the shade for the experimental period. The data shown in Table 1 illustrates the number of dead slugs in each tub (out of a sample size of 10), and the slug feeding, during the observation period.

TABLE 1

| Treatment | TUB 1 Day 4 | TUB 1 Day 10 | TUB 2 Day 4 | TUB 2 Day 10 | Total Kill |
|---|---|---|---|---|---|
| 3.92% Iron IDS | 1/10 no feeding | 4/9* | 1/10 no feeding | 5/9 | 11/20 (55%) |
| 8.0% Iron IDS | 0/10 no feeding | 4/10 | 0/10 light feeding | 2/10 | 6/20 (30%) |
| 12.0% Iron IDS | 0/10 heavy feeding | 3/10 | 0/10 light feeding | 2/10 | 5/20 (25%) |
| 0.56% Iron/ 3.5% NaIDS | 3/10 no feeding | 6/7 | 4/10 no feeding | 6/6 | 19/20 (95%) |
| 0.80% Iron/ 5.0% NaIDS | 7/10 no feeding | 2/3 | 2/10 no feeding | 6/8 | 17/20 (85%) |
| Control | 0/10 | 0/10 | 0/10 | 0/10 | 0/20 (0%) |

*The day 10 results indicate the number of dead slugs out of the number of slugs remaining after day 4.

EXAMPLE 2

Iron IDS was made by complexing the liquid NaIDS (Baypure CX100/34) with iron sulfate. The mixture was then dry blended into a cereal flour (wheat), and prepared as described above. The mixture was then dry blended into 96.08% cereal flour (wheat) and sugar, and prepared as described above.

Two test tubs were set up, each tub containing 10 *Arion ater* and one young potted lettuce plant. Compost soil was used to cover the tub bottoms. The slugs were collected from the Mt. Newton Seed Orchard, and added to the tubs. Each tub received 7.5 grams of bait scattered over the soil. The tubs were kept outside in the shade for the experimental period. The data shown in Table 2 illustrates the number of dead slugs in each tub (out of a sample size of 10), and the slug feeding, during the observation period.

TABLE 2

| Treatment | TUB 1 Day 4 | TUB 1 Day 10 | TUB 2 Day 4 | TUB 2 Day 10 | Total Kill |
|---|---|---|---|---|---|
| 3.92% Iron IDS | 0/10 15% bait eaten | 3/10 10% plant eaten | 0/10 50% bait eaten | 1/10 100% plant eaten | 4/20 (20%) |
| 8.0% Iron IDS | 0/10 10% bait eaten | 2/10 50% plant eaten | 0/10 20% bait eaten | 1/10 0% plant eaten | 3/20 (15%) |
| 12.0% Iron IDS | 0/10 15% bait eaten | 2/10 150% plant eaten** | 0/10 15% bait eaten | 1/10 50% plant eaten | 3/20 (15%) |
| 0.56% Iron/ 3.5% NaIDS | 0/10 95% bait eaten | 9/10 0% plant eaten | 2/10 85% bait eaten | 6/8 0% plant eaten | 17/20 (85%) |
| 0.80% Iron/ NaIDS | 0/10 30% bait eaten | 1/10 0% plant eaten | 1/10 65% bait eaten | 6/9 0% plant eaten | 8/20 (40%) |
| Control | 0/10 | 0/10 | 0/10 | 0/10 | 0/20 (0%) |

**A second plant was added after the first plant was eaten.

Those having ordinary skill in the art will know, or be able to ascertain, using no more than routine experimentation, many equivalents to the specific embodiments of the invention described herein. These and all other equivalents are intended to be encompassed by the following claims. All publications and references cited herein including those in the background section are expressly incorporated herein by reference in their entirety.

What is claimed is:

1. A terrestrial mollusc stomach poison composition, comprising:
   a carrier material edible to molluscs; and
   a second component having
   a transition metal compound selected from the group consisting of a transition metal protein, a transition metal carbohydrate, a transition metal salt, and combinations thereof, and
   a complexing agent selected from the group consisting of iminodisuccinic acid, complexes of iminodisuccinic acid, and salts thereof.

2. The composition of claim 1, wherein the molar ratio of the transition metal compound to the complexing agent is in the range of 1:0.02 to 1:20.

3. The composition of claim 1, wherein the transition metal compound is present in an amount such that the transition metal concentration is in the range of about 200–90,000 ppm.

4. The composition of claim 1, wherein the complexing agent is present at a concentration in the range of 2000 to 140,000 ppm.

5. The composition of claim 1, wherein the transition metal compound is present in an amount such that the transition metal concentration is in the range of about 2000 to 10,000 ppm and the complexing agent is present at a concentration in the range of about 7,000 to 120,000 ppm.

6. The composition of claim 1, wherein the transition metal compound is selected from the group consisting of a saccharated transition metal oxide, a transition metal albuminate, a transition metal ammonium citrate, transition metal chlorides, a transition metal citrate, a transition metal gluconate, a transition metal lactate, a transition metal phosphate, a transition metal pyrophosphate, a transition metal nitrate, a transition metal sulfate, a transition metal stearate, and a transition metal tartrate.

7. The composition of claim 6, wherein the transition metal of the transition metal compound is selected from the group consisting of iron and copper.

8. The composition of claim 1, wherein the carrier is selected from the group consisting of wheat cereal, agar, gelatin, oil cake, pet food wheat, soya, oats, corn, rice, fruits, fish by-products, sugars, coated vegetable and cereal seeds, casein, blood meal, bone meal, yeast, and fats.

9. A terrestrial mollusc stomach poison composition, comprising:
   a carrier material edible to molluscs; and
   an effective amount of a complex of a transition metal compound and a complexing agent, the complexing agent being selected from the group consisting of iminodisuccinic acid, complexes of iminodisuccinic acid and salts thereof.

10. The composition of claim 9, wherein the transition metal compound is associated with the complexing agent.

11. The composition of claim 9, wherein the complexing agent comprises a chelating agent, and wherein the transition metal is chelated by the chelating agent to form a chelate.

12. The composition of claim 11, wherein the chelating agent is D,L-aspartic acid, N-(1,2-dicarboxyethyl), tetrasodium salt.

13. The composition of claim 11, wherein the chelate is selected from the group consisting of an iron chelate and a copper chelate.

14. The composition of claim 13, further comprising a carrier selected from the group consisting of wheat cereal, agar, gelatin, oil cake, pet food wheat, soya, oats, corn, rice, fruits, fish by-products, sugars, coated vegetable and cereal seeds, casein, blood meal, bone meal, yeast, paper products, clay, and fats.

15. The composition of claim 12, wherein the chelate is present in an amount such that the transition metal concentration is in the range of about 200–90,000 ppm.

16. A method of exterminating molluscs, comprising the steps of:
 providing a molluscicidal composition comprising
  a carrier material edible to molluscs
  a transition metal compound selected from the group consisting of a transition metal protein, a transition metal carbohydrate, and a transition metal salt; and
  a complexing agent selected from the group consisting of iminodisuccinic acid, complexes of iminodisuccinic acid, and salts thereof;
 applying the molluscicidal composition to an area infested with molluscs; and
 allowing the molluscs to ingest the molluscicidal composition.

17. The method of claim 16, wherein the transition metal compound is selected from the group consisting of a saccharated transition metal oxide, a transition metal albuminate, a transition metal ammonium citrate, transition metal chlorides, a transition metal citrate, a transition metal gluconate, a transition metal lactate, a transition metal phosphate, a transition metal pyrophosphate, a transition metal nitrate, a transition metal sulfate, a transition metal stearate, and a transition metal tartrate.

18. The method of claim 17, wherein the transition metal of the transition metal compound is selected from the group consisting of iron and copper.

19. The method of claim 17, wherein the transition metal of the transition metal compound is iron.

20. A method of exterminating molluscs, comprising the steps of:
 providing a molluscicidal composition comprising
  a carrier material edible to molluscs, and
  an effective amount of a complex of a transition metal compound and a complexing agent, the complexing agent being selected from the group consisting of iminodisuccinic acid, complexes of iminodisuccinic acid, and salts thereof;
 applying the molluscicidal composition to an area infested with molluscs; and
 allowing the molluscs to ingest the molluscicidal composition.

21. The method of claim 20, wherein the complex is selected from the group consisting of an iron complex and a copper complex.

22. The method of claim 20, wherein the transition metal of the transition metal compound is iron.

* * * * *